US006309863B1

(12) United States Patent
Anderson et al.

(10) Patent No.: US 6,309,863 B1
(45) Date of Patent: Oct. 30, 2001

(54) METHODS FOR GENERATING PHOSPHORYLATION SITE-SPECIFIC IMMUNOLOGICAL REAGENTS

(75) Inventors: Carl W. Anderson, Stony Brook, NY (US); Ettore Appella; Kazuyasu Sakaguchi, both of Montgomery, MD (US)

(73) Assignee: Brookhaven Science Associates, Upton, NY (US)

(*) Notice: Subject to any disclaimer, the term of this patent is extended or adjusted under 35 U.S.C. 154(b) by 0 days.

(21) Appl. No.: 09/236,415

(22) Filed: Jan. 25, 1999

(51) Int. Cl.[7] .............................. C07K 16/00; C12P 21/04
(52) U.S. Cl. ..................... 435/70.21; 436/547; 436/548; 530/387.9; 530/388.1; 530/388.2; 530/389.1; 530/413
(58) Field of Search ........................ 435/70.21; 436/547, 436/548; 530/387.9, 413, 388.1, 388.2, 389.1

(56) References Cited

U.S. PATENT DOCUMENTS

| | | | |
|---|---|---|---|
| 4,543,439 | * 9/1985 | Frackelton et al. | 436/548 |
| 5,580,742 | * 12/1996 | Bodenmueller et al. | 435/7.94 |
| 5,599,681 | * 2/1997 | Epstein et al. | 435/7.23 |
| 5,814,459 | * 9/1998 | Montminy | 435/7.1 |

OTHER PUBLICATIONS

Sakaguchi et al., *Genes and Dev.* 12: 2831–2841 (1998).
Matsui et al., *J. Cell Biol.* 140: 647–657 (1998).
Burke et al., *Biochem. Biophys. Res. Commun.* 204: 129–134 (1994).
Chen et al., *Biochem. Biophys. Res. Commun.* 216: 976–984 (1995).
Otaka et al., *Tetrahedron Letters* 36: 927–930 (1995).
Akamatsu et al., *Bioorg. & Med. Chem.* 5: 157–163 (1997).
Conrad et al., *Hybridoma* 16: 167–173 (1997).
Matsumara et al., *J. Cell Biol.* 140: 119–129 (1998).
Ginty, et al., "Regulation of CREB Phosphorylation in the Suprachiasmatic Nucleus by Light and a Circadian Clock", *Science* 260, 1993, 238–241.
Ginty, et al., "Nerve Growth Factor Activates a Ras–Dependent Protein Kinase that Stimulates c–fos Transcription via Phosphorylation of CREB", *Cell* 77, 713–725.
Miyoshi, et al., "Practical Phosphopeptide Synthesis Using Dimethylphosphono Amino Acids (No. 2)", *Peptide Chemistry* 33, 25–28.
Shieh, et al., "DNA Damage–Induced Phosphorylation of p53 Alleviates Inhibition by MDM2", *Cell* 91, 325–334.
Siliciano, et al., "DNA Damage Induces Phosphorylation of the Amino Terminus of p53", *Genes & Development* 11, 3471–3481.

* cited by examiner

Primary Examiner—David Saunders
(74) Attorney, Agent, or Firm—Margaret C. Bogosian

(57) ABSTRACT

The present invention provides methods for generating phosphorylation site-specific immunological reagents. More specifically, a phosphopeptide mimetic is incorporated into a polypeptide in place of a phosphorylated amino acid. The polypeptide is used as antigen by standard methods to generate either monoclonal or polyclonal antibodies which cross-react with the naturally phosphorylated polypeptide. The phosphopeptide mimetic preferably contains a non-hydrolyzable linkage from the appropriate carbon atom of the amino acid residue to a phosphate group. A preferred linkage is a $CF_2$ group. Such a linkage is used to generate the phosphoserine mimetic $F_2Pab$, which is incorporated into a polypeptide sequence derived from p53 to produce antibodies which recognize a specific phosphorylation state of p53. A $CF_2$ group linkage is also used to produce the phosphothreonine mimetic $F_2Pmb$, and to produce the phosphotyrosine mimetic, $F_2Pmp$.

32 Claims, 4 Drawing Sheets

Tyrosine

Phosphotyrosine $H_2Pmp$      $F_2Pmp$

Analogues of Phosphotyrosine

FIG. 1

Analogues of Phosphoserine and Phosphothreonine

FIG. 2

Analogues of Phosphotyrosine

SEQUENCE LISTING

```
<160> NUMBER OF SEQ ID NOS: 10

<210> SEQ ID NO: 1
<211> LENGTH: 15
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 1

Pro Leu Xaa Gln Glu Thr Ala Pro Leu Xaa Gln Glu Thr Ala Cys
  1               5                  10                  15

<210> SEQ ID NO: 2
<211> LENGTH: 13
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 2

Met Gly Glu Pro Gln Xaa Asp Pro Ser Val Glu Pro Cys
  1               5                  10

<210> SEQ ID NO: 3
<211> LENGTH: 13
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 3

Pro Gln Ser Asp Pro Xaa Val Glu Pro Pro Leu Ser Cys
  1               5                  10

<210> SEQ ID NO: 4
<211> LENGTH: 13
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 4

Glu Pro Pro Leu Xaa Gln Glu Thr Phe Ser Asp Leu Cys
```

<210> SEQ ID NO: 5
<211> LENGTH: 13
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 5

Ser Gln Glu Thr Phe Xaa Asp Leu Trp Lys Leu Leu Cys
 1               5                  10

<210> SEQ ID NO: 6
<211> LENGTH: 14
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 6

Pro Glu Asn Asn Val Leu Xaa Pro Leu Pro Ser Gln Ala Cys
 1               5                  10

<210> SEQ ID NO: 7
<211> LENGTH: 13
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 7

Leu Ser Pro Leu Pro Xaa Gln Ala Met Asp Asp Leu Cys
 1               5                  10

<210> SEQ ID NO: 8
<211> LENGTH: 13
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 8

Asn Asn Thr Ser Ser Xaa Pro Gln Pro Lys Lys Lys Cys
 1               5                  10

<210> SEQ ID NO: 9
<211> LENGTH: 15
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 9

-continued

```
Cys Lys Lys Gly Gln Ser Thr Xaa Arg His Lys Lys Leu Met Phe
 1               5                  10                  15
```

<210> SEQ ID NO: 10
<211> LENGTH: 9
<212> TYPE: PRT
<213> ORGANISM: Artificial Sequence
<220> FEATURE:
<223> OTHER INFORMATION: Description of Artificial Sequence: POLYPEPTIDE
      ANTIGEN
<220> FEATURE:
<223> OTHER INFORMATION: Residue Xaa is a phosphoserine mimetic

<400> SEQUENCE: 10

```
Cys Phe Lys Glu Gly Pro Asp Xaa Asp
 1               5
```

METHODS FOR GENERATING PHOSPHORYLATION SITE-SPECIFIC IMMUNOLOGICAL REAGENTS This invention was made with Government support under contract number DE-AC02-98CH10886, awarded by the U.S. Department of Energy. The Government has certain rights in the invention.

BACKGROUND OF THE INVENTION

Protein phosphorylation is important in the regulation of a wide variety of cellular processes. Regulation of protein activity by phosphorylation of serine, threonine, and tyrosine residues is highly utilized. Histidine, arginine, and lysine residues on proteins are also phosphorylated by cellular processes, but the significance is unknown due to the difficulty of studying these highly unstable modifications. The detection and quantitation of changes in the phosphorylation state of a protein is of great utility in the study of its functional significance.

Standard methods for measuring the state of protein phosphorylation typically involve prelabeling of the added phosphate moiety by incorporation of a radioactive isotope of phosphorous (as a phosphate). Such phosphorylation assays suffer from several methodological pitfalls, including health risks and disposal problems associated with the high amounts of [$^{32}$P]Pi required for the prelabeling experiments, the bother of working with regulated substances, and a lack of site specificity when several sites are phosphorylated in one protein or peptide moiety. As a result of these drawbacks, immuno-chemical based methods for detecting protein phosphorylation state are increasing in popularity. The degree of sensitivity and selectivity achievable with immuno-chemical methodology makes it an attractive alternative (Matsui et al., *J. Cell. Bio.* 140: 647–657 (1998); Conrad et al., *Hybridoma* 16: 167–173 (1997)).

Phosphorylation state-dependent monoclonal antibodies specific for a variety of cytoskeletal proteins have been produced and characterized. These antibodies were isolated by immunization protocols in which the specific targeting of phosphorylated epitopes was not the primary objective. More recently, small synthetic phosphopolypeptides have been used to improve the chance of targeting antibody production to epitopes on the phosphorylation sites (Sakaguchi et al., *Genes and Dev.* 12: 2831–2841 (1998); Matsui et al., *J. Cell Bio.* 140: 647–657 (1998); Chen et al., *FASEB J.* 2: A550 (1988); Czernik et al., *Methods in Enzymology* 201: 264–283 (1991)). While more direct, this method still suffers from the limitation of rapid dephosphorylation of the polypeptide antigen upon immunization which reduces the titer of phospho-specific antibodies. This is particularly a problem when using antigen containing phosphoserine and phosphothreonine, both of which usually are considerably less stable than phosphotyrosine.

SUMMARY OF THE INVENTION

The present invention provides methods for generating antibodies which specifically react to a polypeptide phosphorylated at a particular amino acid. Methods for generating both monoclonal and polyclonal antibodies are provided. The method involves providing a polypeptide which has an incorporated mimetic of the phosphorylated amino acid residue. The mimetic has antigenic determinants also present on the naturally phosphorylated amino acid. The polypeptide antigen is used by standard methods to generate either monoclonal or polyclonal antibodies which cross-react with the natural phosphorylated polypeptide, and specifically recognize a specific phosphorylation state of the polypeptide.

In one embodiment, the mimetics contains a non-hydrolyzable linkage between the carbon atom and the phosphorous atom (of the phosphate group). In a preferred embodiment, this linkage is a $CF_2$ group. Incorporation of this linkage group into phosphoserine produces the mimetic $F_2$Pab. $F_2$Pab is used in place of phosphoserine in a polypeptide sequence derived from p53 to produce antibodies which recognize a specific phosphorylation state of p53. In another embodiment, the $CF_2$ linkage group is incorporated into phosphothreonine to produce the mimetic $F_2$Pmb. In another embodiment the $CF_2$ linkage is incorporated into phosphotyrosine to produce the mimetic $F_2$Pmp.

DETAILED DESCRIPTION OF THE INVENTION

The present invention is based in part on the discovery that phosphopeptide mimetics previously used as phosphatase inhibitors (Burke et al., *Biochem. Biophys. Res. Commun.* 204: 129–134 (1994); Chen et al., *Biochem. Biophys. Res. Commun.* 216: 976–984)) are antigenic. More specifically, a mimetic incorporated into a polypeptide which is then used to inoculate an animal to evoke an immune response, elicits antibodies to antigenic determinants located at least in part on the mimetic. The present invention is also based on the discovery that the antibodies generated against the mimetic cross-react with the natural phosphopeptide. This cross-reactivity indicates that mimetics possess antigenic determinants highly similar to those of the natural phosphopeptide, when presented in the context of the same flanking amino acids. The antibodies generated to the mimetic-peptide have sufficient binding activity and specificity for the natural phosphorylated polypeptide to serve as tools in immuno-diagnostic identification of the phosphoprotein from which the antigenic amino acid sequence was derived. These discoveries have lead to the present invention which provides methods for producing and isolating immunological reagents which identify a particular phosphorylation state of a predetermined protein.

The chemical structure of a phosphopeptide mimetic appropriate for use in the present invention must closely approximate the natural phosphorylated residue which is mimicked, and must also be chemically stable (e.g. resistant to dephosphorylation by phosphatases). This is achieved with a synthetic molecule that comprises the amino acid atomic structure with a non-hydrolyzable linkage to a phosphate moiety, in lieu of the naturally occurring oxygen bridge. In a preferred embodiment, a $CF_2$ group links the amino acid to the phosphate. Mimetics of several amino acids which are phosphorylated in nature can be generated by this approach. Mimetics of phosphoserine, phosphothreonine, and phosphotyrosine are generated by placing a $CF_2$ linkage from the appropriate carbon to the phosphate moiety. In a preferred embodiment, the mimetic molecule L-2-amino-4-(diethylphosphono)-4,4-difluorobutanoic acid ($F_2$Pab) substitutes for phosphoserine (Otaka et al., Tetrahedron Letters 36: 927–930 (1995)), (Sakaguchi et al., Genes and Dev. 12: 2831–2841 (1998)). Experiments presented in the Exemplification section indicate that polypeptide antigens with $F_2$Pab incorporated in place of the natural phosphoserine, can also be used in the method of the present invention, to generate phosphospecific antibodies. These polypeptide antigens, listed below, are designated by SEQ ID NOS: 2–10.

```
Pro-Leu-F₂Pab-Gln-Glu-Thr-Ala-Pro-Leu-F₂Pab-Gln-Glu-Thr-Ala-Cys    SEQ ID NO: 1

Met-Gly-Glu-Pro-Gln-F₂Pab-Asp-Pro-Ser-Val-Glu-Pro-Cys              SEQ ID NO: 2

Pro-Gln-Ser-Asp-Pro-F₂Pab-Val-Glu-Pro-Pro-Leu-Ser-Cys              SEQ ID NO: 3

Glu-Pro-Pro-Leu-F₂Pab-Gln-Glu-Thr-Phe-Ser-Asp-Leu-Cys              SEQ ID NO: 4

Ser-Gln-Glu-Thr-Phe-F₂Pab-Asp-Leu-Trp-Lys-Leu-Leu-Cys              SEQ ID NO: 5

Pro-Glu-Asn-Asn-Val-Leu-F₂Pab-Pro-Leu-Pro-Ser-Gln-Ala-Cys          SEQ ID NO: 6

Leu-Ser-Pro-Leu-Pro-F₂Pab-Gln-Ala-Net-Asp-Asp-Leu-Cys              SEQ ID NO: 7

Asn-Asn-Thr-Ser-Ser-F₂Pab-Pro-Gln-Pro-Lys-Lys-Lys-Cys              SEQ ID NO: 8

Cys-Lys-Lys-Gly-Gln-Ser-Thr-F₂Pab-Arg-His-Lys-Lys-Leu-Met-Phe      SEQ ID NO: 9

Cys-Phe-Lys-The-Glu-Gly-Pro-Asp-F₂Pab-Asp                          SEQ ID NO: 10
```

Figure 1:
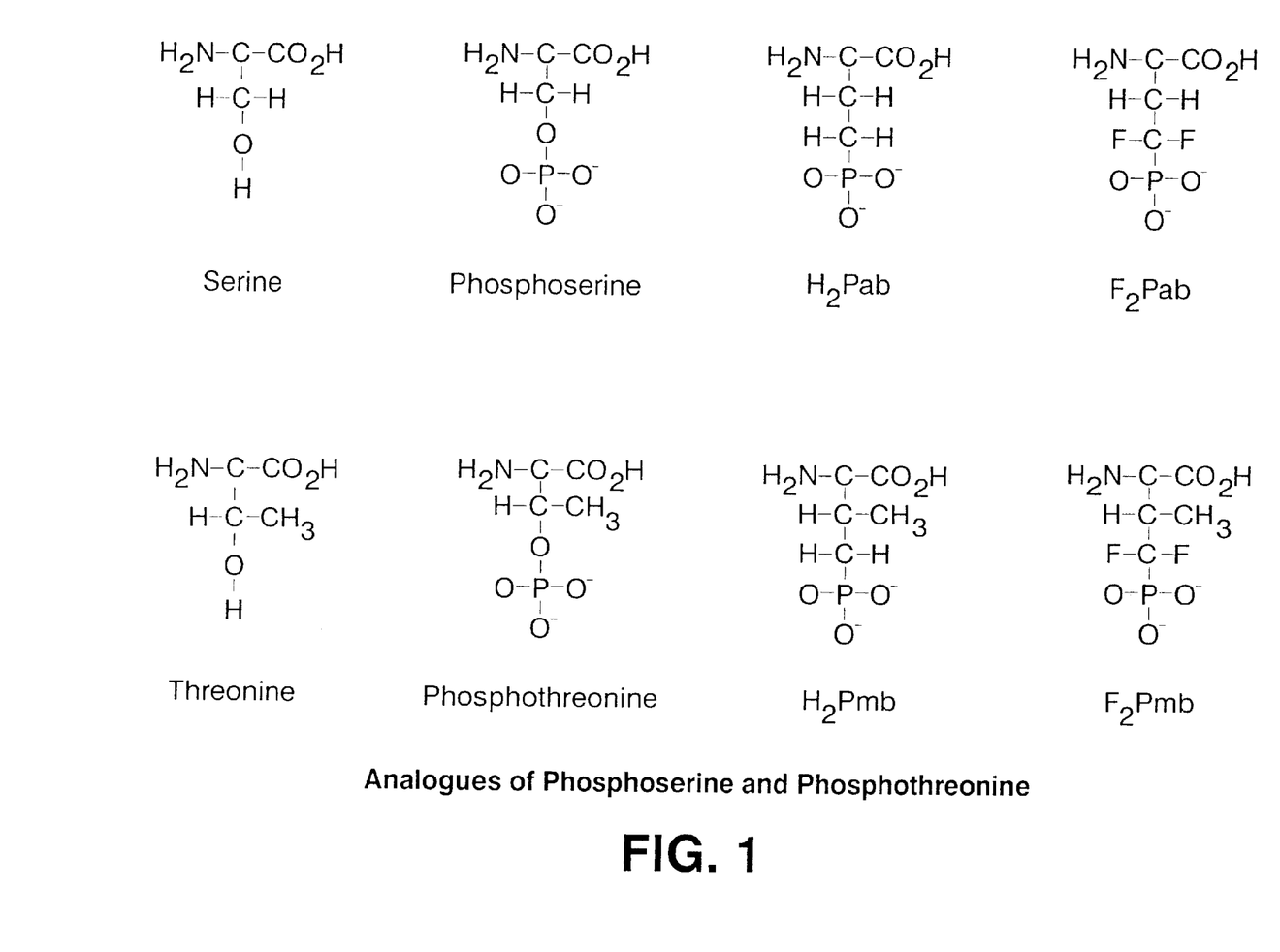
FIG. 1 represents analogues of phosphoserine and phosphothreonine.
Figure 2:
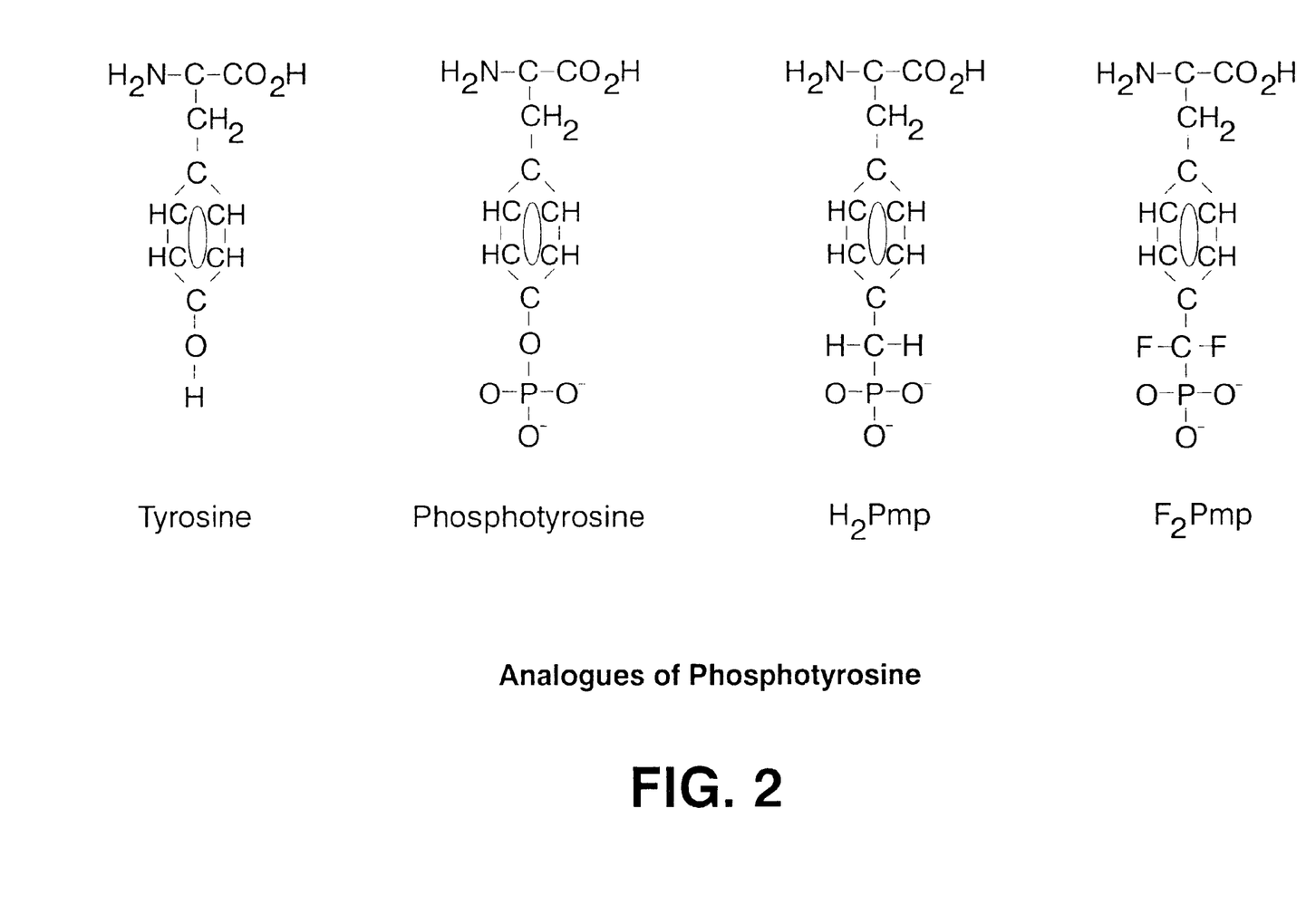
FIG. 2 represents analogues of phosphotyrosine.

L-2-amino-4-phosphono-4,4-difluoro-3-methylbutanoic acid ($F_2$Pmb) substitutes for phosphothreonine, and L-2-amino-4-phosphono(difluoromethyl) phenylalanine ($F_2$Pmp) substitutes for phosphotyrosine (Akamatsu et al., Bioorg & Med Chem. 5: 157–163 (1997)) in an antigenic polypeptide (FIG. 1 and FIG. 2). In an alternate embodiment, the oxygen bridge of the natural amino acid is replaced with a methylene group (FIG. 1 and 2).

The synthesis of $F_2$Pab is described by Otaka et al., Tetrahedron Lett. 36: 927–930 (1995). The synthesis of $F_2$Pmp is described by Smyth et al., Tetrahedron Lett. 35: 551 (1994) and Akamatsu et al., Bioorg. & Med. Chem. 5: 157–163 (1997). Synthesis of $F_2$Pmb is accomplished by methods analogous to $F_2$Pab synthesis, using a backbone precursor that has one additional methyl group.

To generate immunological reagents specific for a predetermined phosphoprotein, the appropriate mimetic(s) is incorporated into a synthetic peptide which corresponds to the sequence surrounding the phosphorylated residue(s). Methods for this incorporation are known or otherwise available to one of skill in the art. The length of sequence required for the generation of phospho-specific antibodies may depend upon the particular phosphoprotein of study. Generally the presence of sequence corresponding to 3 or 4 residues flanking the phospho residue is sufficient to generate the required specificity. In one embodiment, the polypeptide antigen comprises a tandem repeat of this sequence with the appropriate mimetic incorporated. Spacer amino acids can be incorporated between the repeated sequence to facilitate antigen processing and presentation. The polypeptide can be produced by chemical synthesis by one of skill in the art through the application of routine experimentation. As detailed in the Exemplification section which follows, a polypeptide antigen with the amino acid sequence specified by SEQ ID NO: 1, listed below, can be used to generate polyclonal antibodies which recognize p53 phosphorylated at serine 15. Several phosphopeptides corresponding to other natural serine phosphorylation sites of p53 have been successfully used to generate phospho-specific antibodies The mimetic-containing polypeptide may be further modified to more closely resemble the natural product or, alternatively, to promote antigenicity. Such modifications include, but are not limited to, enzymatic modifications, chemical protection or deprotection, denaturation and chemical coupling. In a preferred embodiment, the polypeptide is coupled to the carrier protein, keyhole limpet hemocyanin. Other carrier proteins can be substituted including for example, bovine serum albumin, ovalbumin and purified protein derivative of tuberculin. Chemical coupling may be achieved, for example using any bifunctional reagent.

Once produced and appropriately modified, the polypeptide antigen is used to inoculate an animal under conditions which elicit an immune response. Products of the immune response are isolated and screened for components cross-reactive with antigenic determinants otherwise unique to the phosphoprotein. These components are isolated and used as reagents to identify a particular phosphorylation state of the protein from which the polypeptide antigen sequence was derived.

Immunization of the animal used to produce the immunological reagents is generally performed as a timed series of inoculations. In a preferred embodiment, the natural phosphopeptide-conjugate is used in one or more final inoculations (boosts). This step is intended to increase the number of B cells that make the most useful antibodies without unduly stimulating synthesis of antibodies reactive with the unphosphorylated peptide which results from stimulation of antibody synthesis by the dephosphorylated peptide. These boosts are performed according to conventional techniques, and can be further optimized empirically.

One aspect of the present invention is a method for generating and isolating polyclonal antibodies which bind specifically to a protein or polypeptide which is phosphorylated at a predetermined amino acid residue, using phosphopeptide mimetics incorporated into polypeptides as antigen. Polyclonal antibodies are prepared by immunizing an animal with immunogen prepared as described above, using conventional techniques (see e.g., Harlow and Lane (Eds.), *Antibodies, A Laboratory Manual* (Cold Spring Harbor Laboratory, Cold Spring Harbor, N.Y. (1988)). Briefly, the immunized animal is maintained under conditions whereby antibodies reactive with the immunogen are produced. Blood is collected from the animal upon reaching a desired antibody titer. The serum, containing the antibodies, is separated from the other blood components. Alternatively, antibody containing ascitic fluid can be induced and isolated from the immunized animal. The polyclonal antibody-containing serum or ascitic fluid can optionally be further separated into fractions of particular types of antibodies (e.g., IgG or IgM).

Because the peptide antigen used contains antigenic determinants common to both the phospho- and unphosphorylated protein, the serum generated by this method usually contains a subset of antibodies which specifically bind the phosphoprotein, and also a subset of antibodies which bind independent of phosphorylation state. Such unwanted binding activities can be cleared or depleted from the antiserum by conventional techniques (Czernik et al., *Methods in Enzymology* 201: 264–283 (1991)). When necessary, monospecific antibodies can be purified from the serum using the antigenic determinant in affinity purification (e.g. by affinity chromatography) or conversely, by depleting the serum of all other antibody activity.

Another aspect of the present invention is a method for generating and isolating monoclonal antibodies which bind specifically to a predetermined phosphoprotein epitope, using phosphopeptide mimetics incorporated into polypeptides as antigen. Monoclonal antibody secreting hybridomas are produced using the antigen described above in conventional techniques (see e.g., Harlow and Lane (Eds.), *Antibodies, A Laboratory Manual* (Cold Spring Harbor Laboratory, Cold Spring Harbor, N.Y. (1988)). In a preferred embodiment, phospho-specific monoclonal antibodies are produced by murine hybridomas formed by fusion of: a) a mouse myeloma or hybridoma which does not secrete antibody with, b) a murine spleen cell which secretes antibodies, obtained from a mouse immunized with a mimetic-containing polypeptide antigen.

Typically, several mice are immunized with a primary injection of antigen followed by a number of boosting injections. During or after the immunization procedure, sera from the mice are screened to identify mice which have mounted a substantial immune response. For selected mice, the spleen cells are obtained and fusions are performed. Suitable fusion techniques include, for example, the Sendai virus technique (Kohler and Milstein, *Nature* 256: 495 (1975)), or the polyethylene glycol method (Kennet, "*Monoclonal Antibodies, Hybridomas—A New Dimension in Biological Analysis*", Eds. Kennet, McKern and Bechtol, Plenum Press, NY (1980)).

The hybridomas that result are then screened for production of antibodies specific for the antigen. Several assays can be used for screening and can be performed with either the phosphomimetic-polypeptide antigen or the naturally phosphorylated-polypeptide antigen. A suitable screening technique is a solid phase radioimmunoassay. A solid phase is prepared by coupling the appropriate antigen to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive to antigen.

The monoclonal antibodies can be produced in large quantities by injecting antibody producing hybridomas into the peritoneal cavity of mice and after an appropriate time, harvesting ascitic fluid from the mice. The monoclonal antibodies are then isolated from the fluid. Alternatively, the antibodies can be produced by culturing the hybridomas in vitro and isolating secreted monoclonal antibodies from the culture medium directly.

Methods of the present invention described above can be used to produce immunological reagents specific for either a known or a suspected protein phosphorylation state. When specific for a known phosphorylation state, the antibodies can be used to closely monitor protein phosphorylation under various conditions (e.g. cell cycle, hormonal stimulation, or stress). Alternatively, phospho-specific antibodies are produced to a suspected naturally occurring phosphorylation state. These immunological reagents can be used to confirm or rule out the physiological occurrence of a suspected phosphorylation state.

Results presented in the Exemplification section, which follows, indicate that the methods of the present invention, described above, also result in the isolation of antibodies which bind a particular phosphoresidue, independent of flanking amino acid sequences. Such antibodies arise when produced as either monoclonal or polyclonal antibodies. These antibodies exhibit binding to the particular phosphoresidue largely independent of the flanking amino acid sequence. The antibodies can be identified and, when necessary, purified by their ability to bind to phosphoresidues of polypeptide sequences unrelated to the initial antigen. Such antibodies provide valuable research tools. One use of these antibodies is in an immuno-based kinase assay which is applicable to a wide range of proteins.

It will be recognized by one of skill in the art that the teachings of the present invention can be applied to the isolation of phospho-specific antibodies produced by systems other than those described above, through the application of merely routine experimentation. One such example is the use of a mimetic containing antigen to screen a combinatorial library for antibodies that exhibit binding activity. The present disclosure is intended to encompass this and related applications.

EXEMPLIFICATION

Generation of Polyclonal Antibodies.

Antibodies specific for p53 phosphorylated at serine 15 were affinity purified from hyperimmune serum by passing the serum over a series of polypeptide linked columns. An initial passage of the serum over a column containing a polypeptide of p53 residues 11–22, phosphorylated at serine 15, enriched for p53 specific antibodies. The bound antibodies were eluted and then cleared of antibodies not specific for phosphoserine by passage over a column containing the unphosphorylated p53 polypeptide. The flow-through was retained and characterized.

Figure 3:
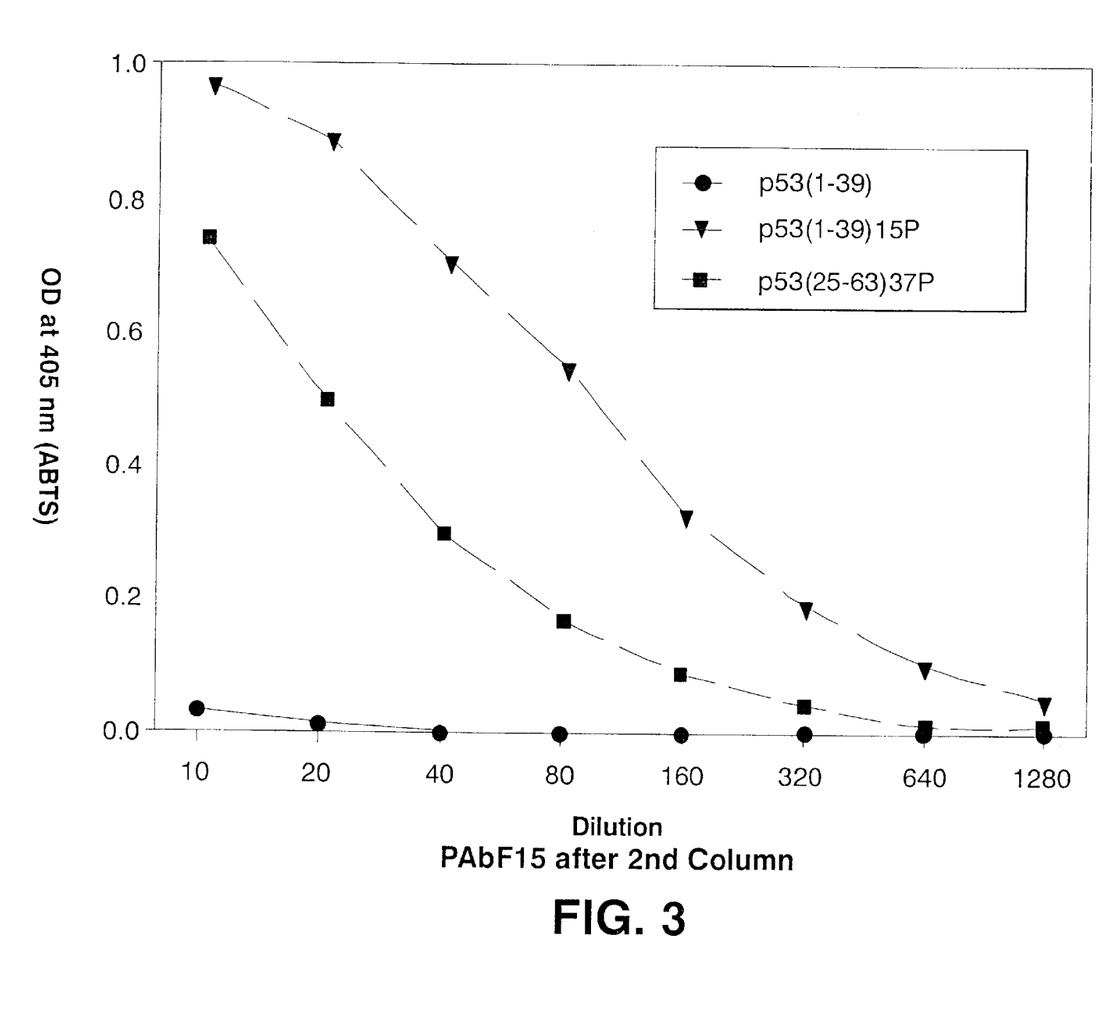
FIG. 3 is a diagrammatic representation of data from an ELISA using the affinity-purified pAbF15 antibody after passage through a (p53(Ac-11-22)Cys) column to deplete antibodies which cross-react with the unphosphorylated peptide.

Binding specificity of the resulting antiserum was determined by enzyme-linked immunosorbent assay (ELISA) using the polypeptides p53(1–39), p53(1–39)15P, and p53(25–63)37P. Specific binding to both the phosphorylated polypeptides was detected at antibody dilutions less than 1:320 (FIG. 3), with more binding to p53(1–39)15P, at all concentrations. Binding to non-phosphorylated polypeptide was insignificant at all concentrations. The cross-reactivity of the antiserum to the p53(25–63)37P polypeptide indicated the presence of non-specific phosphoserine antibodies.

Figure 4:
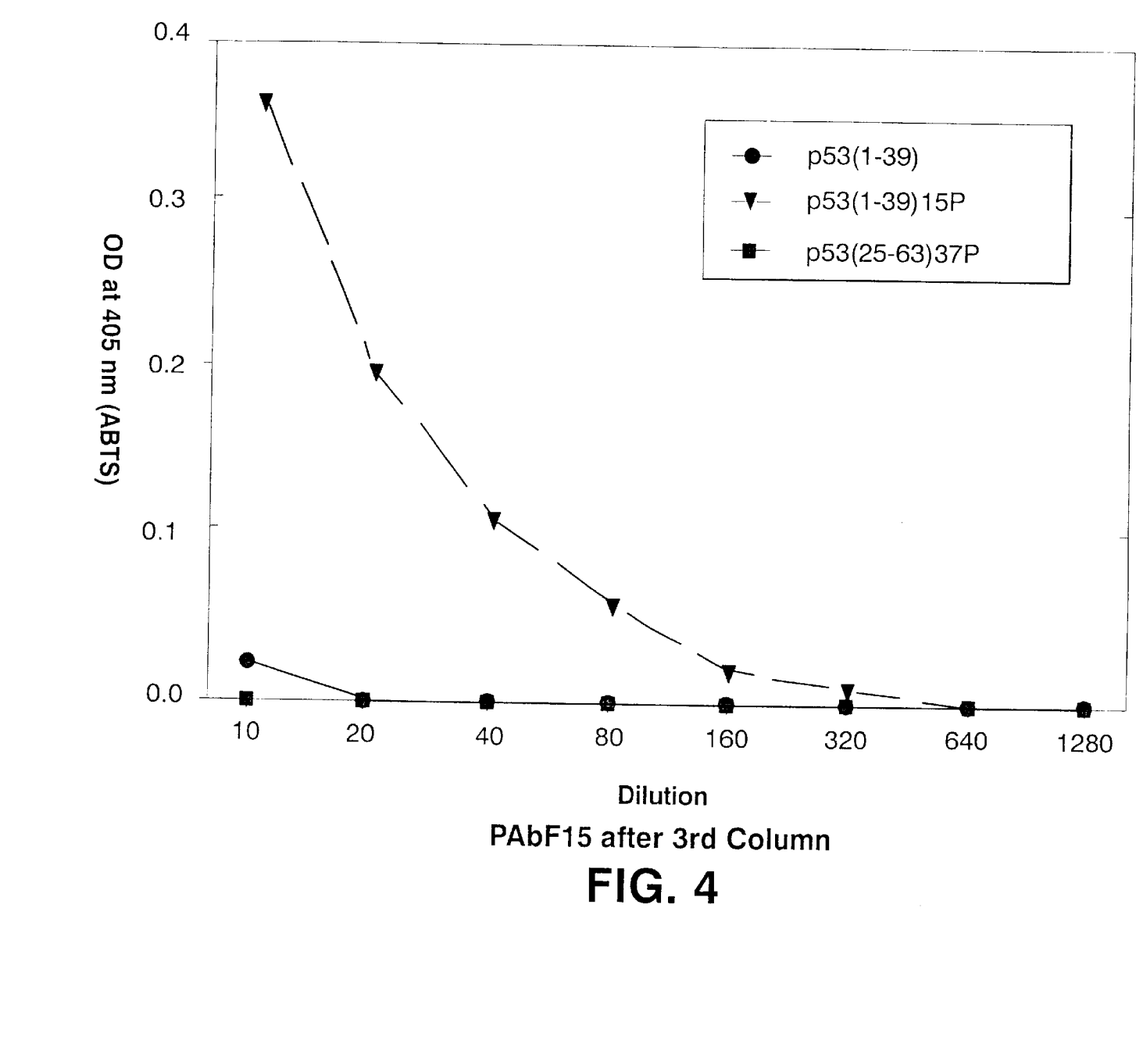
FIG. 4 is a diagrammatic representation of data from an ELISA using the affinity-purified pAbFl5 antibody after passage through a (p53(Ac-32-43)(37P)Cys) column to deplete antibodies which cross-react with p53 phosphorylated at serine 37.

To clear the antiserum of non-specific phosphoserine antibodies the antiserum was passed over a column of p53(Ac-32-43(37P)Cys). The resulting unbound flow-through was tested as above and found to be highly specific for p53 phosphorylated at serine 15 (FIG. 4). Reactivity and specificity for the p53 serine 15 was confirmed by immunoblot analysis using unphosphorylated p53 and p53 that was enzymatically phosphorylated at serine 15 by the protein kinase DNA-PK.

The generation of antibodies that specifically recognize naturally phosphorylated polypeptides, from peptide antigen with $F_2$Pab substituted for phosphoserine, demonstrates that $F_2$Pab functions as an effective phosphoserine mimic when used as antigen. Importantly, these results also indicate that peptides into which $F_2$Pab is incorporated, when used as antigen, undergo the necessary antigen processing and presentation required for the induction of B-lymphocytes in the production of specific antibodies. The results presented above indicate that $F_2$Pab incorporated into an antigen can be used to generate antibodies that specifically recognize a particular site of phosphorylation within a peptide, and also antibodies with a broader recognition of phosphoserines in general.

The successful generation of polyclonal antibodies specific for phosphoserines, using the $F_2$Pab mimic described here, indicates that immunization of mice or other animals with polypeptides containing $F_2$Pab, by otherwise standard methods, will also result in the stimulation and clonal expansion of B-lymphocytes to produce antibodies specific for a naturally phosphorylated residue, polypeptide, or protein. Such B-lymphocytes can be isolated and used in the production of hybridomas to generate monoclonal antibodies specific for phosphoproteins.

Methods of the Invention

Production of Immune Serum. The polypeptide used as antigen is specified by SEQ ID NO: 1. The polypeptide consists of fifteen residues, the sequence corresponding to a seven amino acid sequence of p53 amino acid residues 13–19, being repeated twice and containing the phosphoserine mimic $F_2$Pab in place of serine 15, the polypeptide having an additional carboxy-terminal cysteine residue in addition to the p53 amino acid sequence. The polypeptide was chemically synthesized using t-Boc chemistry on an Applied Biosystems 430A peptide synthesizer according to manufacturer recommendations, except that Boc-$F_2$Pab (Et2)-OH was manually coupled using t-Boc chemistry. The assembly of the peptide chain was by standard methods (*Synthetic Peptides*, G. Grant (Ed.), W. H. Freeman & Co., New York (1992)). Cleavage of the peptide from the resin and removal of the side-chain protecting groups were carried out using a two-step deprotection method (Otaka et al., *Tetrahedron Lett*. 36: 927–930 (1995)). The peptides were purified by high pressure liquid chromatography (HPLC) on a Vydac C-8 column with 0.05% TFA/water-acetonitrile.

The polypeptide was coupled through the carboxy-terminal cysteine residue to keyhole limpet hemocyanin (KLH). The resulting KLH-$F_2$Pab-peptide conjugate was used to immunize a rabbit by standard procedures. Briefly, the rabbit was injected subcutaneously with 500 μg of the peptide conjugate mixed with adjuvant on days 0, 7, and 14. Complete Freund's adjuvant was used for the first injection, and Incomplete Freund's adjuvant was used for additional injections. Blood was collected on day 21. After day 21, immunization and blood collection was repeated weekly for five weeks.

Generation of Polypeptides for Affinity Chromatography. Polypeptides of 13 amino acids corresponding to the human p53 sequence of residues 11 to 22, and having an additional carboxy-terminal cysteine residue, were chemically synthesized by standard methods as non-phosphorylated: (p53(Ac-11-22Cys)); or as phosphorylated at serine 15: (p53(Ac-11-22(15P)Cys)). Polypeptide corresponding to the human p53 sequence of residues 32 to 43 with an added carboxy-terminal cysteine residue, was synthesized as phosphorylated at serine 37: (p53(Ac-32-43(37P)Cys)).

Peptides were synthesized by the solid phase method with Fmoc chemistry (*Synthetic Peptides*, G. Grant (Ed.), W. H. Freeman & Co., New York (1992)) using an Applied Biosystems 430A peptide synthesizer (Foster City, Calif.). Phosphoserine residues were incorporated as Fmoc-Ser(PO(OBzl)OH)—OH (Novabiochem, San Diego, Calif.) (Wakamiya et al., *Chem. Lett*. 6: 1099–1102 (1994)). Cleavage of the peptide from the resin and removal of the side-chain protecting groups were carried out using reagent K (TFA:phenol:thioanisole:$H_2$O:EDT=82.5:5:5:5:2.5) for 3 hours at room temperature (King et al., *Int. J. Pept. Protein Res*. 36: 255–266 (1990)). The peptides were purified by HPLC on a Vydac C-8 column (Hesperia, Calif.) with 0.05% TFA/water-acetonitrile, or on a pH-stable Vydac C-8 column (Hesperia, Calif.) with 0.2% hexafluoroacetone-$NH_4OH$, pH 7.0/acetonitrile (for 1–39 peptides). The mass of peptides were confirmed by electrospray ionization mass spectrometry on a Finnigan MAT SSQ 7000 (Finnigan MAT, San Jose, Calif.).

Generation of Polypeptide Linked Columns. The polypeptides (p53(Ac-11-22Cys)), (p53(Ac-11-22(15P)Cys)), and (p53(Ac-32-43(37P)Cys)) were coupled to Sulfolink (Pierce Chemical Co.) according to the instructions provided by the manufacturer. The resulting Sulfolink conjugates were used to create three columns, each packed with one of the polypeptide—Sulfolink conjugates.

Affinity Purification. Antibodies specific for p53 phosphorylated at serine 15 were purified from hyperimmune rabbit serum by affinity chromatography using a series of peptide linked columns. The serum was first passed through a (p53(Ac-11-22(15P)Cys)) column. After washing, the adsorbed antibodies were eluted with ImmunoPure IgG Elution Buffer (Pierce Chemical Co.), and were immediately neutralized by adding 1 M Tris buffer (pH 9.5). Eluate was passed over a (p53(Ac-11-22Cys) column to remove antibodies that bound unphosphorylated p53. The unbound flow-through was collected and then passed over a (p53 Ac-32-43)(37P)Cys) column to deplete it of antibodies that bind to phosphoserines irrespective of their position within a polypeptide.

Antibody Analysis. Affinity purified antibody preparations were characterized for binding to the polypeptides p53(1–39), p53(1–39)15P, or p53(1–39)37P by ELISA assay, as described in the Pierce Chemical Technical Library and in Engvall et al., *Immunochemistry* 8: 871–875 (1971). Plates were coated with the indicated polypeptide by diluting the polypeptide into sodium carbonate-bicarbonate buffer, pH 9.6 (1.59 g $Na_2CO_3$, 2.93 g $NaHCO_3$ per liter, pH adjusted with HCL) to 1 μg/ml and 50 or 100 ng (50 or 100 μl) was incubated at 4° C. overnight or for about 3 hours at room temperature. The peptide solution was then removed and plates were blocked by incubation with 1% BSA in PBS for 1 hour at room temperature. Polypeptide-coated wells were incubated with antibody dilutions between 1/10 and 1/1000. Bound antibody was detected by incubation with horseradish peroxidase (HRP)-conjugated anti-rabbit IgG antibody, followed by addition of the HRP substrate ABTS (2,2'-azinobis(3-ethylbenzthiazoline-6-sulfonic acid)). HRP oxidation of the ABTS produced a green color product which was used to identify antibody presence. The amount of rabbit IgG bound to the polypeptide-coated plate was determined by measuring the optical density of the mixture at 405 nm ($OD_{405}$). Results were confirmed by separate ELISA assay and spot blots ("western" blots).

Polypeptides used in the ELISA analysis were synthesized by Fmoc chemistry as described above. Longer peptides were synthesized by a fragment condensation method (Sakamoto et al., *Int. J. Peptide Protein Res.* 48: 429–442 (1996)).

What is claimed is:

1. A method for isolating polyclonal antibodies which bind specifically to a phosphorylated polypeptide which is phosphorylated at a particular amino acid, comprising:
  a) providing a synthetic polypeptide comprising a mimetic of the particular amino acid which is phosphorylated, the synthetic polypeptide being formulated in a physiologically acceptable carrier;
  b) immunizing an animal with the synthetic polypeptide of step a);
  c) collecting and preparing serum or ascitic fluid from the immunized animal of step b);
  d) screening for the presence of antibodies specific for the phosphorylated polypeptide; and
  e) when necessary, further enriching for antibodies specific for the phosphorylated polypeptide through conventional methods.

2. The method of claim 1 wherein binding of the polyclonal antibodies to the phosphorylated polypeptide is dependent on amino acid sequences which flank the particular amino acid which is phosphorylated.

3. The method of claim 1 wherein binding of the polyclonal antibodies to the phosphorylated polypeptide is independent of amino acid sequences which flank the particular amino acid which is phosphorylated.

4. The method of claim 1 wherein antibodies specific for the phosphorylated polypeptide are further enriched by affinity purification.

5. The method of claim 1 wherein antibodies specific for the phosphorylated polypeptide are further enriched by depleting co-mingled antibodies which exhibit undesired binding activities.

6. The method of claim 1 wherein the animal is further immunized with a natural phosphopeptide-conjugate comprised of an appropriate amino acid sequence, as a boost.

7. The method of claim 1 wherein the synthetic polypeptide of step a) is modified prior to immunization step b).

8. The method of claim 7 wherein the synthetic polypeptide is modified through coupling to a carrier protein selected from the group consisting of keyhole limpet hemocyanin (KLH), bovine serum albumin (BSA), ovalbumin and purified protein derivative of tuberculin (PPD), using any bifunctional reagent.

9. The method of claim 1 wherein the particular amino acid which is phosphorylated is selected from the group consisting of serine, threonine and tyrosine.

10. The method of claim 1 wherein the mimetic contains a non-hydrolyzable linkage from a carbon atom to a phosphate group.

11. The method of claim 10 wherein the non-hydrolyzable linkage comprises a $CF_2$ group.

12. The method of claim 10 wherein $F_2Pab$ is a mimetic for phopsphoserine.

13. The method of claim 10 wherein $F_2Pmp$ is a mimetic for phosphotyrosine.

14. The method of claim 10 wherein $F_2Pmb$ is a mimetic for phosphothreonine.

15. The method of claim 1 wherein the synthetic polypeptide of step a) comprises an amino acid sequence derived from amino acid sequences of p53.

16. The method of claim 15 wherein the synthetic polypeptide is as specified in SEQ ID NO: 1.

17. The method of claim 15 wherein the synthetic polypeptide is selected from the group consisting of SEQ ID NOS: 2, 3, 4, 5, 6, 7, 8, 9, and 10.

18. A method for isolating monoclonal antibodies which bind specifically to a phosphorylated polypeptide which is phosphorylated at a particular amino acid, comprising:
  a) providing a synthetic polypeptide comprising a mimetic of the particular amino acid which is phosphorylated, the synthetic polypeptide being formulated in a physiologically acceptable carrier;
  b) immunizing an animal with the synthetic polypeptide of step a);
  c) collecting B-cells from the animal of step b)
  d) generating hybridomas by fusing the B-cells of step c) with myeloma cells;
  e) screening the hybridomas of step d) for antibodies which bind specifically to the phosphorylated polypeptide;
  f) isolating and propagating hybridomas identified in step e); and
  g) isolating monoclonal antibodies from the isolated and propagated hybridomas of step f).

19. The method of claim 18 wherein binding of the monoclonal antibodies to the phosphorylated polypeptide is dependent on amino acid sequences which flank the particular amino acid which is phosphorylated.

20. The method of claim 18 wherein binding of the monoclonal antibodies to the phosphorylated polypeptide is independent of amino acid sequences which flank the particular amino acid which is phosphorylated.

21. The method of claim 18 wherein the animal is further immunized with a natural phosphopeptide-conjugate comprised of an appropriate amino acid sequence, as a boost.

22. The method of claim 18 wherein the synthetic polypeptide of step a) is modified prior to the immunization step b).

23. The method of claim 22 wherein the synthetic polypeptide is modified through coupling to a carrier protein selected from the group consisting of keyhole limpet hemocyanin (KLH), bovine serum albumin (BSA), ovalbumin and purified protein derivative of tuberculin (PPD), using any bifunctional reagent.

24. The method of claim 18 wherein the particular amino acid which is phosphorylated is selected from the group consisting of serine, threonine and tyrosine.

25. The method of claim 18 wherein the mimetic contains a non-hydrolyzable linkage from a carbon atom to a phosphate group.

26. The method of claim 25 wherein the non-hydrolyzable linkage comprises a $CF_2$ group.

27. The method of claim 25 wherein $F_2$Pab is a mimetic for phopsphoserine.

28. The method of claim 25 wherein $F_2$Pmp is a mimetic for phosphotyrosine.

29. The method of claim 25 wherein $F_2$Pmb is a mimetic for phosphothreonine.

30. The method of claim 18 wherein the synthetic polypeptide of step a) comprises an amino acid sequence derived from amino acid sequences of p53.

31. The method of claim 30 wherein the synthetic polypeptide is as specified in SEQ ID NO: 1.

32. The method of claim 30 wherein the synthetic polypeptide is selected from the group consisting of SEQ ID NOS: 2, 3, 4, 5, 6, 7, 8, 9, and 10.

* * * * *